United States Patent [19]

Hawman

[11] Patent Number: 4,849,638
[45] Date of Patent: * Jul. 18, 1989

[54] SINGLE-FOCUS COLLIMATOR AND SCINTILLATION CAMERA SYSTEM AND METHOD FOR USING IT

[75] Inventor: Eric G. Hawman, Buffalo Grove, Ill.

[73] Assignee: Siemens Gammasonics, Inc., Des Plaines, Ill.

[*] Notice: The portion of the term of this patent subsequent to Sep. 27, 2005 has been disclaimed.

[21] Appl. No.: 28,650

[22] Filed: Mar. 20, 1987

[51] Int. Cl.⁴ ............................................. G01T 1/166
[52] U.S. Cl. .......................... 250/363.02; 250/363.10; 378/4
[58] Field of Search .......... 250/363 SH, 363 S, 505.1; 378/4, 10, 12, 19, 20, 147, 149

[56] References Cited

U.S. PATENT DOCUMENTS

| | | | |
|---|---|---|---|
| 3,509,341 | 4/1970 | Hindel et al. | 250/363 SH |
| 3,777,148 | 12/1973 | Miraldi | 250/363 SH |
| 4,095,107 | 6/1978 | Genna et al. | 250/363.02 |
| 4,295,047 | 10/1981 | Koga et al. | 250/363.02 |
| 4,389,569 | 6/1983 | Hattori et al. | 250/363.02 |
| 4,584,478 | 4/1986 | Genna et al. | 250/363.02 |
| 4,774,410 | 9/1988 | Hsieh | 250/363.02 |

OTHER PUBLICATIONS

Proceedings of 10th Annual Symposium of the Society of Nuclear Medicine, Jan., 1980, pp. 147-157, Zimmerman et al.
Nuclear Medicine Communications, 1980, vol. 1, pp. 94-101, Jarritt et al.
IEEE Transactions on Medical Imaging, vol. MI-1, No. 1, Jul. 1982, pp. 63-67, Rogers et al.
IEEE Transactions on Nuclear Science, vol. NS-29, No. 1, Feb., 1982, pp. 520-523, Hirose et al.
IEEE Transactions on Nuclear Science, vol. NS-24, No. 1, Feb. 1977, pp. 581-583, Knoll et al.

Primary Examiner—Janice A. Howell
Assistant Examiner—William R. Rauchhol
Attorney, Agent, or Firm—Mark H. Jay

[57] ABSTRACT

A collimator is in the shape of a closed curve and has one and only one focal point. The collimator is dimensioned such that, in use, the focal point may be positioned inside the body organ to be imaged. The focal point is caused to densely trace over the body organ of interest to form a tomographic image in less time, without imaging the rest of the body slice.

16 Claims, 4 Drawing Sheets

SINGLE-FOCUS COLLIMATOR AND SCINTILLATION CAMERA SYSTEM AND METHOD FOR USING IT

BACKGROUND OF THE INVENTION

The invention relates to scintillation cameras, and more particularly relates to scintillation camera systems which are used to produce a tomographic image. In particular, the invention relates to SPECT tomography of relatively small body organs such as the heart. Reference is made to U.S. Pat. No. 4,774,410.

In conventional tomographic imaging, a focusing collimator is set up so that the focal point is located outside the patient's body, at such a distance that the region of focus is just large enough to include the entire body slice to be imaged. Then, the camera head is rotated 360° around the body to ensure full sampling. Thereafter, each image of the slice is backprojected, and all of the backprojected images are filtered and added together to produce a final tomographic image of the slice.

Annular focusing collimators are known, but in the conventional annular focusing collimator the collimator is made up of a plurality of identical sections, each having its own individual focal point which is located outside the region of interest. Where, for example, an annular collimator has three sections, it may be regarded as three individual camera heads which are mounted together and simultaneously rotated like a multi-head camera. However, in all cases such collimators have a plurality of focal points which during use are all located outside the region of interest.

To avoid artifacts caused by truncation, an image of for example an entire slice through the torso is a necessary by product of any attempt to merely image for example the heart. As a result, a small body organ such as the heart cannot be faithfully imaged without imaging the entire body slice in which the heart is contained.

Since the heart is relatively small as compared with the torso, production of an image of the heart can be accomplished only by a wasteful use of computer resources, which must be used to image the entire slice rather than merely imaging the particular region of interest.

It would be advantageous to provide a scintillation camera system which could produce an image of a relatively small body organ such as the heart without devoting equal effort to imaging other parts of the body which are not of interest.

In accordance with the invention, there is provided a collimator which has the shape of a closed curve. Within each plane of interest the collimator has one and only one focal point. The focal point is located inside the interior region of the collimator. Advantageously, the dimensions of the collimator are chosen such that during use the focal point is positioned inside the region of interest.

One major advantage of this focusing scheme is that the information which appears at the outer periphery of the collimator directly represents a "backprojected" image value (or layergram) which is to be associated with each location of the focal point. Therefore, it is unnecessary to acquire a plurality of images about that point and to backproject them using a computer. For each point, all necessary information is acquired at one time.

Also, because there is essentially complete sampling about the focal point, it is possible to reconstruct an image of an organ such as the heart with a preferentially enhanced signal-to-noise ratio relative to the organ's surroundings. This can be done by moving the focal point in such a manner that it dwells on the organ longer than it dwells on adjacent body regions.

Another advantage of the invention comes about because of the fixed relationship between each point on the scintillator and the focal point. In a conventional SPECT camera a plurality of photodetectors are mounted to a common scintillator and coordinates of a scintillation flash must be located within the scintillator. This is because there is no unique association between points on the scintillator and points in the region of interest; each point on the scintillator receives radiation from many points within the object of interest and the origin of a particular for example gamma ray cannot be determined from the location where it produces a scintillation. However, in the invention, most radiation detected emanates from the focal point, or from locations near it. Furthermore, for each location of the focal point, the information represented by the detected radiation is a weighting of the image values of all of the points in the object.

Since the weighting function itself is determined by the radial ray pattern and the angular beam dispersion of the collimator, as seen from each point on the detector, it follows that for a perfect collimator (i.e. one with an infinitesimally small beam width) the weighting function is inversely proportional to the distance from the focal point, and is not a function of any other variable. Consequently, within each plane of interest, the angular position of a scintillation about the focal point is unimportant. This eliminates the need for much of the weighting circuitry needed to localize a scintillation flash when conventionally focusing collimators are utilized.

Furthermore, the invention makes it possible to increase the speed of the imaging process. There are two reasons for this. First, the collimator completely surrounds the patient and thus receives radiation from a full 360° of arc. Second, the image data is acquired with focal point inside the object of interest. Because the focal point is the point of highest sensitivity, the focal geometry of the invention is more efficient than the focal geometries of know SPECT systems.

In principle, the invention may be regarded as a tomographic imager that works by using techniques normally employed in planar scanners.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 1:
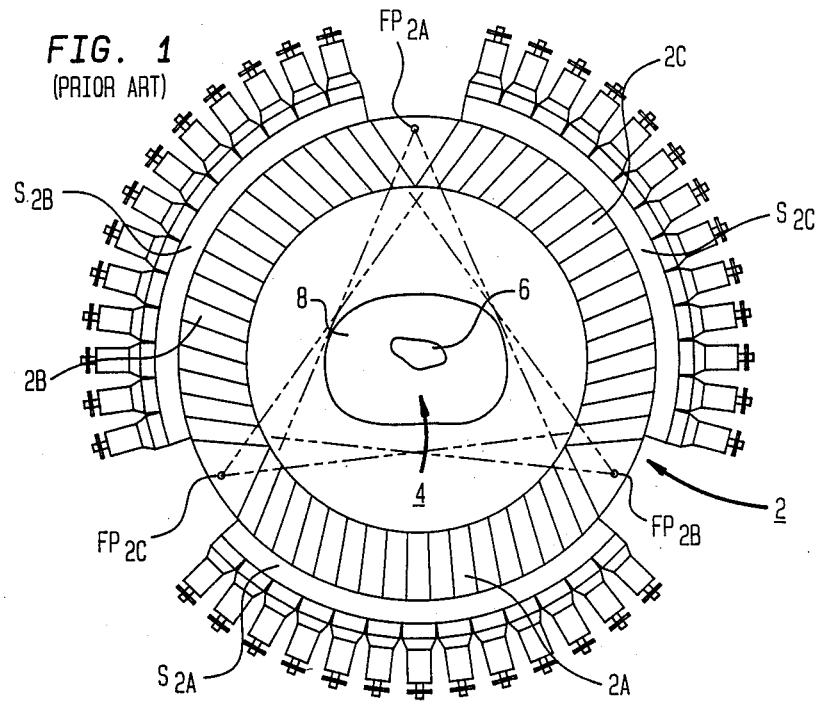
FIG. 1 is a schematic illustration of a annular collimator of a known type, which has been shown in exaggerated scale for clarity.

In all the Figures, the same or corresponding elements are indicated by the same or corresponding reference numerals. It will be understood that the Figures are all shown in exaggerated scale to illustrate how the collimators focus. Thus, the individual collimator channels are shown much larger than they would actually appear. The same is true for the photodetectors (here, phototubes) shown in the Figures. Additionally, the following description will implicitly assume that the invention is used in a gamma camera which uses NaI(T1) scintillation material, but this is only preferred and is not essential to the invention.

The operation of a conventional type of annular collimator such as is illustrated in FIG. 1 will be considered first, before discussion of the preferred embodiment. A conventional annular collimator 2 is divided into for example three like sections 2A, 2B and 2C, each subtending 120° of arc and each having its own focal point $FP_{2A}$, $FP_{2B}$, and $FP_{2C}$ which is located outside the patient 4 whose heart 6 is to be imaged. When such a collimator is utilized, it must be rotated through 120° in order to acquire a complete 360° sampling about the object of interest. (In this example, the object of interest is the heart 6 but the invention is not restricted to cardiac imaging.) Each section 2A, 2B and 2C of the collimator has a corresponding scintillator $S_{2A}$, $S_{2B}$ and $S_{2C}$, which in turn is associated with a set of photodetectors; here, the photodetectors are phototubes.

As a practical matter, it is necessary to image not the heart along, but rather an entire slice 8 of the body. This is because radioactive material migrates to regions other than the heart alone, and the body is not symmetrical about the heart 6. For example, in some views of the heart, the heart 6 will be located behind a lung (not shown) while in other views the heart 6 will be behind the spine (not shown). If the final image is not constructed to take these other organs into account, artifacts will be present in the image.

Figure 2:
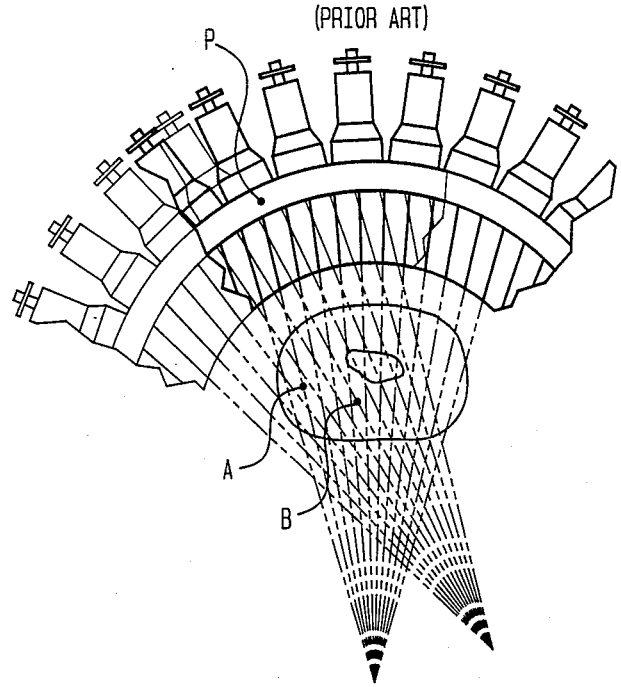
FIG. 2 illustrates the non-unique relationship between points on the scintillator of a conventional scintillation camera and points in the body to be imaged.

Therefore, as is known to those skilled in the art of SPECT, with a conventional focusing annular collimator, a large number of views are acquired during a rotation about the body axis. (In this example, the rotation will be 120°.) Then, each view is backprojected and all the backprojected images are added together to reconstruct the image of the slice of the body which is under investigation.

Where the object of interest is the heart, only a relatively small fraction of the reconstructed image is actually of interest. This is illustrated in FIG. 1; the heart 6 takes up a relatively small fraction (perhaps one-seventh) of the area of a transaxial slice 8 through the body. Furthermore, it is necessary to determine the location of a scintillation flash as precisely as possible. Thus, for example, it is necessary to know the location of the scintillation flash relative to the collimator itself. This is because there is no unique association between each point in the object to be imaged and each point in the scintillator; during the process by which all the views are acquired, each point on the scintillator receives information from many points in the object. This is illustrated in FIG. 2; during data acquisition, point P on the scintillator receives information from points A and B of the body, and the information cannot be traced to points A or B until the entire process of filtering and backprojection is completed.

Figure 3:
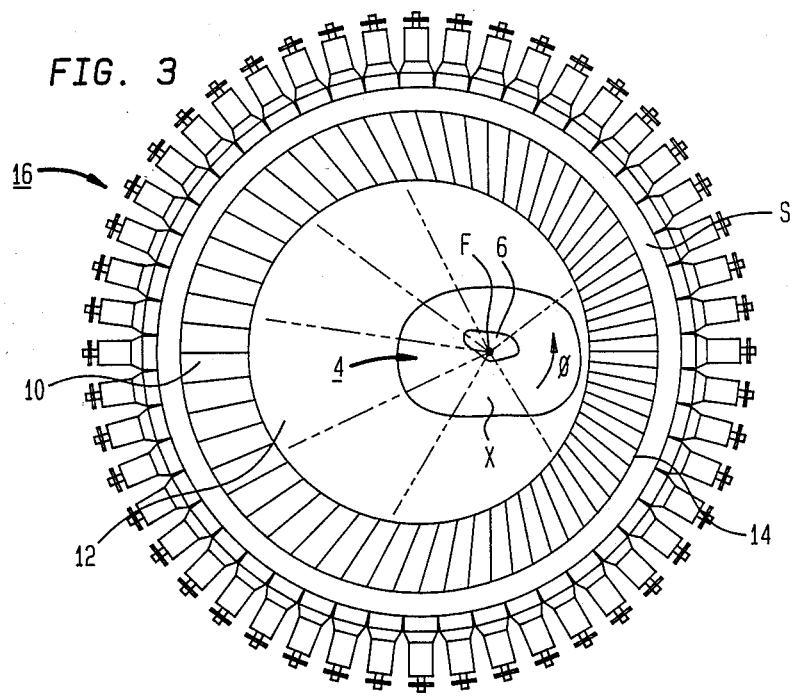
FIG. 3 is a schematic illustration of a preferred embodiment of the invention, shown in exaggerated scale for clarity.

In accordance with the invention, as shown in FIG. 3, the collimator 10 is in the shape of a closed curve, has one and only one focal point F, and is located within a mating scintillator S. The term "closed curve", as used herein, includes all curves which do not intersect themselves and which bound one exterior region and one interior region. Thus, where the closed curve is a circle, the collimator 10 and scintillator S will be annular; where the closed curve is of arbitrary shape, the collimator 10 and scintillator S may have the shape of a meandering path. (Although the scintillator S is shown as a single continuous element, this is merely for clarity. The scintillator S need not be continuous and is advantageously made up of a ring of individual strips of scintillator material. This construction is used because a single annular ring of scintillator material is very expensive.) In this preferred embodiment, the closed curve is a circle and the collimator 10 and scintillator S are annular. The focal point F is located in the interior region 12 of the collimator 10. More specifically, the dimensions of the various parts are such that the focal point F may be positioned inside the body organ to be image (here, the heart 6). As can be seen from FIG. 3, this structure causes the summation of detected radiation which appears around the outer periphery 14 of the collimator 10 to be equivalent to the image value at the focal point F which would result from acquiring multiple individual views of the focal point F and then backprojecting them. Thus, it is only necessary to filter the information which appears at the outer periphery 14 of the collimator 10 because backprojection is intrinsic to the invention. In short, the invention makes a direct determination of the backprojection image (i.e. layergram) at the location of the focal point F.

Figure 5:
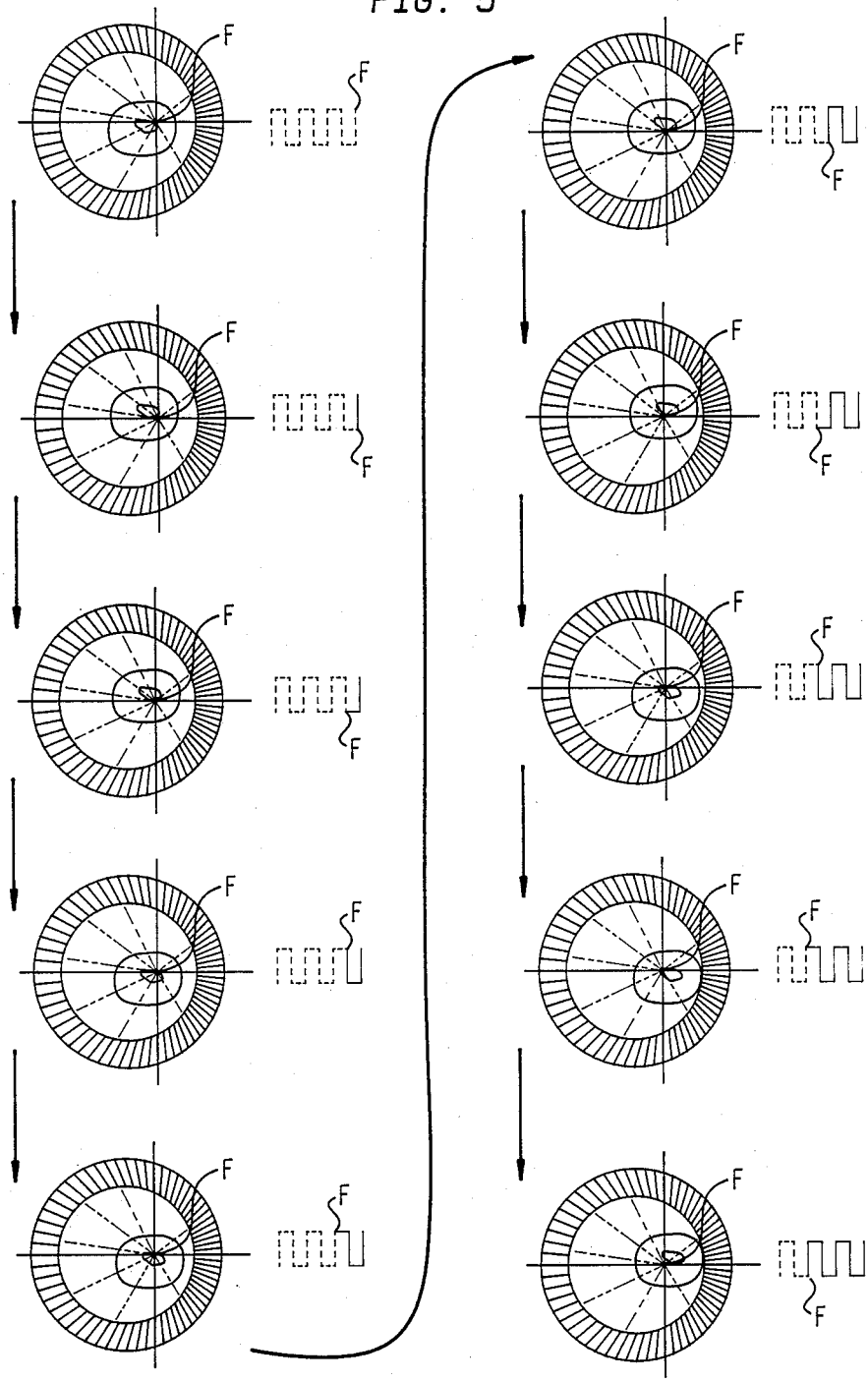
FIG. 5 illustrates another type of motion which can be executed by the preferred embodiment.

In use, after administration of the desired radioisotope to the patient, the focal point F is moved with respect to the patient 4 so that it is traced densely over the region to be imaged (for example, the heart 6) and traced less densely, if at all, over body regions which are not of interest (for example, the region X outside the heart). This can be done by holding the patient 4 fixed and moving the camera head 16, keeping the collimator camera head 16 fixed while moving the patient 4, or moving both the patient 4 and the collimator camera head 16 at the same time. For simplicity, it is now preferred to accomplish this by keeping the patient 4 fixed and moving the camera head 16. Advantageously, where the collimator 10 and scintillator S are annular, the camera head 16 is mounted so as to rotate and translate in a polar coordinate fashion (FIG. 4), but it may be caused to translate in two orthogonal directions (i.e. Cartesian motion, see FIG. 5) if desired. Advantageously, the camera head 16 is moved in a spiral because this requires minimal forces. It is also possible to rotate the collimator 10 within the scintillator S. While each of these alternatives has particular advantages and disadvantages, no one of them is necessary to the practice of the invention; it is only necessary that the focal point F be traced densely enough over the region of interest so that an appropriately detailed image can be formed. FIGS. 4 and 5 do not illustrate the scintillator S and photodetectors because these Figures only show how the collimator 10 moves with respect to the region of interest.

Because backprojection requires a substantial amount of computer resources, it is theoretically possible to produce a tomographic image in less time because the step of backprojection is unnecessary. Additionally, since it is possible to devote more intense investigation to the region of interest, it is unnecessary to spend time producing an image of surrounding body regions which are not of interest.

A further and surprising advantageous result comes about because of the fixed relationship between the points on the scintillator S and the focal point F. In each position of the focal point F, each point on the scintillator S acquires information which, in the main, relates only to the layergram, or backprojection image, at the location of the focal point F. Thus, it is unnecessary for the photodetector structure to have any resolving ability in the $\phi$ direction around the focal point F. This in turn brings about the advantage that the weighting circuitry which is conventionally used to localize scintillation flashes within the scintillators of conventional cameras are unnecessary in the invention.

Figure 6:
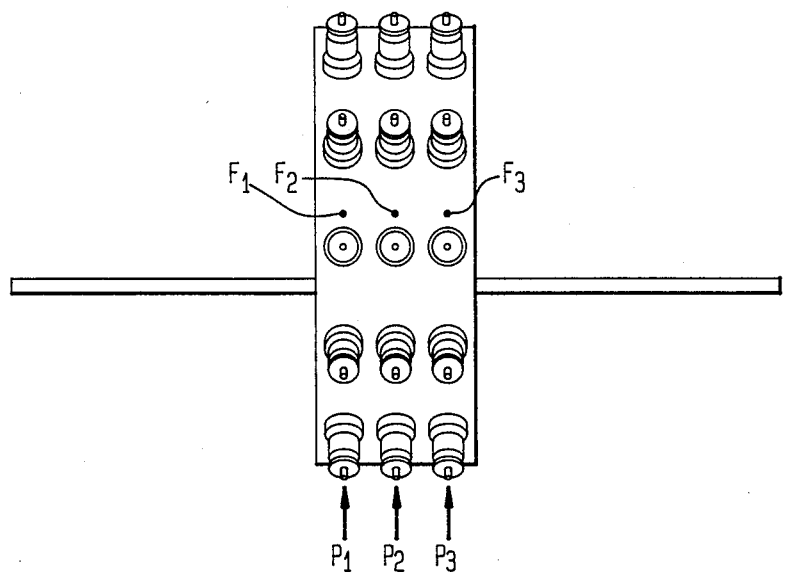
FIG. 6 is a schematic illustration of the preferred embodiment as viewed from the side, shown in exaggerated scale for clarity.
Figure 4A:
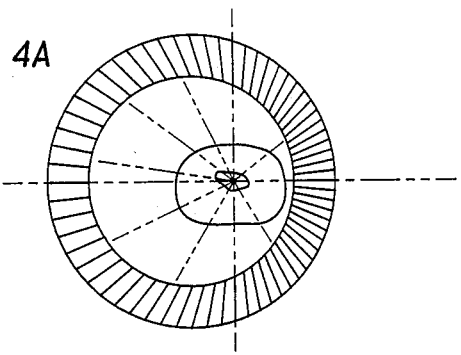
FIGS. 4A–4D illustrates one type of motion which can be executed by the preferred embodiment.
Figure 4B:
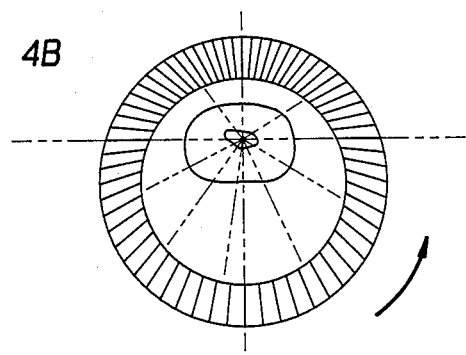
Figure 4C:
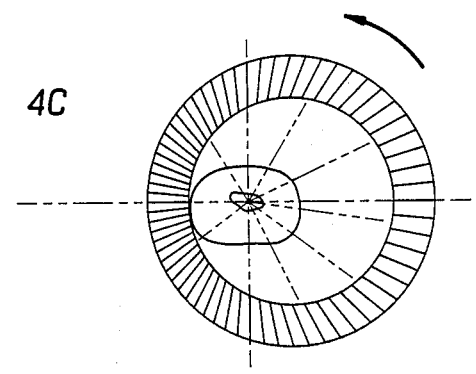
Figure 4D:
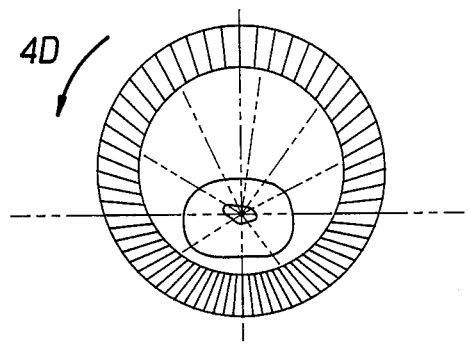

In the preferred embodiment, there are a plurality of image planes. Advantageously, as is shown in FIG. 6, there are three image planes $P_1$, $P_2$ and $P_3$, each having its own focal point $F_1$, $F_2$ and $F_3$ respectively. Further advantageously, the three focal points $F_1$, $F_2$ and $F_3$ are located on a common straight line. This results in the use of three parallel sets of photodetectors which are regularly spaced apart along the body axis of the patient. The patient may be moved parallel to the body axis. There may however be fewer or more image planes of interest, and it also possible to have only one image plane wherein the collimator focuses all radiation to a single point. The choice of the number of focal points, the arrangement of the focal points and the focusing scheme used is determined by the amount of computer resources required, the resolution and imaging time desired, the shape of the collimator and scintillator, and similar tradeoff criteria.

Those skilled in the art will understand that changes can be made in the preferred embodiments here described, and that these embodiments can be used for other purposes. Such changes and uses are within the scope of the invention, which is limited only by the claims which follow.

I claim:

1. A collimator having the shape of a closed curve, the collimator bounding an interior region and, within each image plane of interest, focusing to one and only one focal point located in said interior region.

2. The collimator of claim 1, wherein there are a plurality of image planes of interest and each focal point lies in its corresponding plane of interest.

3. The system of claim 2, where the image planes are parallel and spaced apart at regular intervals.

4. The system of claim 2, further comprising means for producing relative translational movement of said image planes of interest and said body region along an axis of said body region.

5. The collimator of claim 12, wherein the closed curve is a circle and the collimator is annular:

6. A scintillation camera system, comprising:
a collimator having the shape of a closed curve, the collimator bounding an interior region which is large enough to accommodate a body region to be imaged, and, within each image plane of interest, focusing to one and only one focal point located within said body region; and
means for moving said focal point with respect to said body region.

7. The system of claim 6, wherein the closed curve is a circle and the collimator is annular.

8. The system of claim 6, wherein said moving means comprises means for moving the collimator.

9. The system of claim 8, wherein said moving means comprises means for moving the collimator in a polar coordinate system.

10. The system of claim 8, wherein said moving means comprises means for moving the collimator in a Cartesian coordinate system.

11. The system of claim 6, further comprising a scintillator surrounding the collimator and photodetector means surrounding the scintillator.

12. The system of claim 11, wherein said moving means comprises means for moving the scintillator and photodetector means together with the collimator.

13. The system of claim 11, wherein said moving means comprises means for rotating the collimator within the scintillator.

14. The system of claim 6, wherein there are a plurality of image planes of interest.

15. A collimated scintillation camera head, comprising:
a collimator having the shape of a closed curve which has an inner surface and an outer surface, the inner surface bounding an interior region which is large enough to accommodate a body region to be imaged, and the collimator focusing to one and only one focal point located within said body region within each of a plurality of parallel image planes of interest;
scintillator means for converting ionizing radiation into scintillation light, said scintillator means surrounding said collimator and being secured to said outer surface; and
a like plurality of sets of photodetectors, each set of photodetectors lying in a corresponding single one of the image planes and being in optical communication with the scintillator means.

16. A method of imaging a slice of a body organ of interest, comprising the following steps:
placing a radioisotope in said organ;
establishing one and only one focal point which is located in said slice and in said body organ by using a collimator which entirely surrounds said body organ;
acquiring a backprojected image of said point using a scintillator which entirely surrounds said collimator; and
moving said collimator and body organ relative to each other in a manner that said focal point is traced over said body organ within said slice.

* * * * *